US010137177B2

(12) United States Patent
McCarty et al.

(10) Patent No.: US 10,137,177 B2
(45) Date of Patent: Nov. 27, 2018

(54) METHODS AND COMPOSITIONS USED IN TREATING INFLAMMATORY AND AUTOIMMUNE DISEASES

(71) Applicants: Oregon Health & Science University, Portland, OR (US); The United States of America as respresented by the Department of Veterans Affairs, Washington, DC (US)

(72) Inventors: Owen J. McCarty, Portland, OR (US); Norah Verbout, Vancouver, WA (US); Halina Offner-Vandenbark, Portland, OR (US); Erik I. Tucker, Portland, OR (US)

(73) Assignees: Oregon Health & Science University, Portland, OR (US); The United States of America as respresented by the Department of Veterans Affairs, Washington, DC (US)

( * ) Notice: Subject to any disclaimer, the term of this patent is extended or adjusted under 35 U.S.C. 154(b) by 8 days.

(21) Appl. No.: 15/113,200

(22) PCT Filed: Jan. 21, 2015

(86) PCT No.: PCT/US2015/012172
§ 371 (c)(1),
(2) Date: Jul. 21, 2016

(87) PCT Pub. No.: WO2015/112547
PCT Pub. Date: Jul. 30, 2015

(65) Prior Publication Data
US 2017/0007681 A1    Jan. 12, 2017

Related U.S. Application Data

(60) Provisional application No. 61/930,231, filed on Jan. 22, 2014.

(51) Int. Cl.
*A61K 38/48* (2006.01)
*A61K 38/17* (2006.01)
*A61K 9/00* (2006.01)
*A61K 38/16* (2006.01)

(52) U.S. Cl.
CPC ........ *A61K 38/4833* (2013.01); *A61K 9/0019* (2013.01); *A61K 38/16* (2013.01); *A61K 38/177* (2013.01)

(58) Field of Classification Search
None
See application file for complete search history.

(56) References Cited

U.S. PATENT DOCUMENTS 6,706,512 B2 * 3/2004 Gruber ................ C12N 9/6429
435/214

OTHER PUBLICATIONS

Han, May H; et al; "Proteomic analysis of active multiple sclerosis lesions reveals therapeutic targets" Nature, 451, 1076-1081, 2008 (Year: 2008).*
Berry et al., "Thrombin Mutant W215A/E217A Acts as a Platelet GPIb Antagonist," *Arterioscler. Thromb. Vasc. Biol.*, vol. 28:329-334, 2008.
Berry-Lang et al., "Thrombin Mutant W215A/E217A Treatment Improves Neurological Outcome and Reduces Cerebral Infarct Size in a Mouse Model of Ischemic Stroke," *Stroke*, vol. 42:1736-1741, 2011.
Flick et al., "The Development of Inflammatory Joint Disease is Attenuated in Mice Expressing the Anticoagulant Prothrombin Mutant W215A/E217A," *Blood*, vol. 117:6326-6337, 2011.
Langer et al., "Platelets Contribute to the Pathogenesis of Experimental Autoimmune Encephalomyelitis," *Circ. Res.*, vol. 110:1202-1210, 2012.
Verbout et al., "Thrombin Mutant W215A/E217A Treatment Improves Neurological Outcome and Attenuates Central Nervous System Damage in Experimental Autoimmune Encephalomyelitis," *Metab. Brain Dis.*, vol. 30:57-65, 2015.
Verbout et al., "Pharmacological protein C activation improves the neurological outcome of experimental autoimmune encephalomyelitis in mice," Abstract, Keystone Symposia on Molecular and Cellular Biology, Jan. 26, 2014.

* cited by examiner

*Primary Examiner* — David W Berke-Schlessel
(74) *Attorney, Agent, or Firm* — Klarquist Sparkman, LLP

(57) ABSTRACT

Methods of treating neuroinflammation by administration of a selective protein C activator, such as recombinant human WE thrombin and optionally one or more of its cofactors are disclosed. Also disclosed are pharmaceutical compositions for use in the treatment of mammals that exhibit symptoms of neurological inflammation. The pharmaceutical compositions and pharmacological dose comprise a safe and effective amount of WE thrombin.

12 Claims, 5 Drawing Sheets
Specification includes a Sequence Listing.

METHODS AND COMPOSITIONS USED IN TREATING INFLAMMATORY AND AUTOIMMUNE DISEASES

CROSS REFERENCE TO RELATED APPLICATIONS

This is the U.S. National Stage of International Application No. PCT/US2015/012172, filed Jan. 21, 2015, published in English under PCT Article 21(2), which claims the benefit of U.S. Provisional Application No. 61/930,231, filed Jan. 22, 2014, which is herein incorporated by reference in its entirety.

ACKNOWLEDGEMENT OF GOVERNMENT SUPPORT

This invention was made government support under grant mumbers HL095315, HL117589 and HL101972, awarded by the National Institutes of Health. The government has certain rights in the invention.

FIELD

This disclosure concerns the treatment of inflammatory and/or autoimmune diseases. More specifically, this disclosure concerns the treatment of neuroinflammatory diseases, such as multiple sclerosis, with a modified form of recombinant thrombin.

BACKGROUND

Encephalitis is a collective term for acute, remittent or chronic neuroinflammatory diseases of the central nervous system (CNS) characterized by destruction of myelin sheaths, axonal damage, and neuronal injury or death. There are infectious and non-infectious or autoimmune forms of neuroinflammation. Prevalent examples of non-infectious neuroinflammation include Alzheimer's disease, Parkinson's disease, and multiple sclerosis (MS), while more rare forms include amyotrophic lateral sclerosis (ALS), and other chronic neurological disorders. Early pathological findings in the acute/subacute forms of MS point to the inflammation of the blood vessels within the neurovascular unit as the initial pathogenic event. Patients with neuroinflammation, including MS, exhibit permanent functional deficits associated with demyelination and lesion formation. While symptomatic MS patients exhibit some form of neurological deficit, there is variation in clinical presentation, disease course and pathological features. Temporal acute worsening of the symptoms in acute or remittent MS can be particularly devastating. Current treatments of such crises, including corticosteroids or interferon, are reasonably effective; however, some patients show little or no benefit. Despite this heterogeneity, one common feature of MS is blood brain barrier (BBB) disruption, which is linked to clinical relapse. The earliest events associated with BBB disruption is extravasation of immune cells, leakage of blood proteins and activation of microglia. Among the proteins that traverse into the CNS are factors of the blood coagulation cascade.

The pathogenesis of neuroinflammation has been linked to local activation of the coagulation system and deposition of fibrin. Blood vessel injuries are strong promoters of blood coagulation activation and thrombogenesis. Analysis of brain tissue from MS patients has revealed the presence of coagulation proteins, including deposition of fibrin, the product of thrombin mediated cleavage of fibrinogen, within MS lesions and around blood vessels. Among these coagulation proteins are procoagulant enzymes, tissue factor, protein C inhibitor, and fibrinogen. Fibrinogen is a classic acute-phase reactant, containing binding sites for cellular receptors regulating inflammatory processes. It is also a major substrate for the procoagulant serine protease thrombin. Administration of heparin, a direct inhibitor of thrombin, reduces the number of MS exacerbations, suggesting that anticoagulant treatment may be beneficial for MS therapy. Experimental models of neuroinflammation support this approach as either heparin or the direct thrombin inhibitor hirudin is beneficial in experimental autoimmune encephalomyelitis (EAE). Likewise, complementary studies performed in fibrinogen-deficient mice or fibrin depletion by prophylactic administration of anticoagulants or batroxobin have established that fibrin is at least one thrombin substrate that drives EAE disease progression and severity. To date, however, randomized controlled clinical studies have not been conducted to explore the use of anticoagulants to improve the outcome of neuroinflammatory disorders, including MS.

Activated protein C (APC) is a plasma serine protease with anticoagulant properties. APC is generated on the endothelial cell surface by the molecular complex of thrombomodulin and thrombin. In addition to reducing thrombin generation, APC functions as a signaling molecule, exhibiting cytoprotective, anti-inflammatory and anti-apoptotic effects via activation of the protease-activated receptor (PAR)-1 and endothelial protein C receptor (EPCR). In animal models, APC exerts beneficial effects during neuroinflammation in the CNS and periphery, suppressing pro-inflammatory NF-κB signaling and apoptosis in endothelial, neuronal and immune cell populations. Mutant APC analogs with reduced anticoagulant activity also exhibit neuroprotective properties in animal models of CNS injury. Indeed, the ability of exogenous APC administration to reduce neurological deficits and suppress neuroinflammation in the CNS and periphery in EAE indicates that augmenting this pathway may have therapeutic potential for neuroinflammatory disorders, including MS. However, exogenous APC (Drotecogin alfa) is no longer available for clinical evaluation.

SUMMARY

Disclosed herein is a method of treating neuroinflammatory disorders, such as MS, by administering a pharmaceutical composition that includes recombinant human WE (W215A/E217A) thrombin. In some examples, the pharmaceutical composition is formulated to be administered intravenously. In further examples, the pharmaceutical composition is formulated to administer a dose of at least 2.5 µg/kg recombinant WE thrombin to primates or 25 µg/kg to rodents. In still further examples, the recombinant WE thrombin is derived from expression in *E. coli.*

Also disclosed herein are pharmaceutical compositions for use in treating neuroinflammation. Such pharmaceutical compositions include an effective amount of WE thrombin and a pharmaceutically effective carrier. In some examples, the pharmaceutical compositions further include thrombomodulin. In some examples, the pharmaceutical composition is formulated to be administered intravenously. In further examples, the pharmaceutical composition is formulated to deliver a dose of at least 25 μg/kg recombinant WE thrombin to rodents, or 10- to 20-fold less to primates, including humans. In still further examples, the recombinant human WE thrombin is derived from expression in *E. coli.*

The foregoing and other objects, features, and advantages of the invention will become more apparent from the following detailed description, which proceeds with reference to the accompanying figures.

BRIEF DESCRIPTION OF THE DRAWINGS

Some of the drawings in this disclosure are photographic images that may not reproduce properly in a patent application publication. Additionally, some of the photographic images may be better understood using color, which is not available in a patent application publication. Applicants consider all photographic images, including color images part of the original disclosure and reserve the right to present high quality and/or color images of the herein described figures in later proceedings.

SEQUENCE LISTING

Figure 1A:
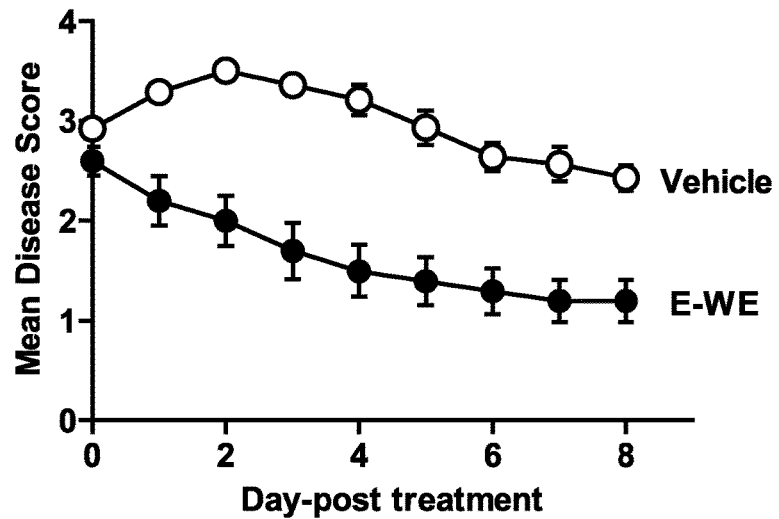
FIG. 1A is a plot of the mean disease scores of MOG/CFA/Ptx immunized mice. At peak disease onset, when clinical scores reached >2.5, mice were treated every other day with vehicle or E-WE thrombin (25 µg/kg; i.v.), as the effective dose of human E-WE is 10 to 20-fold higher in rodents than in primates. Mice were assessed daily and scored as described in the Examples below.

The amino acid sequence listed in the accompanying sequence listing is shown using standard three letter code for amino acids, as defined in 37 C.F.R. 1.822. The Sequence Listing is submitted as an ASCII text file, created on Jul. 19, 2016, 3.0 KB, which is incorporated by reference herein. In the accompanying sequence listing:

SEQ ID NO: 1 is an exemplary WE thrombin amino acid sequence.

DETAILED DESCRIPTION

I. Abbreviations

ALS amyotrophic lateral sclerosis
APC activated protein C
BBB blood brain barrier
CDI cumulative disease index
CNS central nervous system
EAE experimental autoimmune encephalomyelitis
EPCR endothelial protein C receptor
FACS fluorescence activated cell sorting
ICAM intercellular adhesion molecule
MOG myelin oligodendrocyte glycoprotein
MS multiple sclerosis
PAR protease-activated receptor
PMN polymorphonuclear neutrophils
Ptx pertussis toxin
TNF tumor necrosis factor II. Terms and Methods Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell 10 Science Ltd., 1994 (ISBN 0-632-02182-9); and Robert A. Meyers (ed.), Molecular Biology and Biotechnology: a Comprehensive Desk Reference, published by VCR Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes."

In addition, the materials, methods, and examples are illustrative only and not intended to be limiting. In order to facilitate review of the various embodiments of the disclosure, the following explanations of specific terms are provided:

Administration: To provide or give a subject an agent, such as a composition comprising recombinant WE thrombin by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Autoimmune disease: A disorder in which the immune system produces an immune response (e.g. a B cell or a T cell response) against an endogenous antigen, with consequent injury to tissues.

Demyelination: Loss of or damage to myelin, or the impairment in growth or development of the myelin sheath. Demyelination inhibits the conduction of signals in the affected nerves, causing impairment in sensation, movement, cognition, or other functions for which nerves are involved. Demyelinating diseases have a number of different causes and can be hereditary or acquired. In some cases, a demyelinating disease is caused by an infectious agent, an autoimmune response, a toxic agent or traumatic injury. In other cases, the cause of the demyelinating disease is unknown or develops from a combination of factors.

Encephalopathy: A disease or disorder of the brain.

Experimental autoimmune encephalomyelitis (EAE): An animal model of MS (for example, see Gold et al., *Brain* 129:1953-1971, 2006). EAE animals exhibit characteristic plaques of tissue injury disseminated throughout the central nervous system. Plaques show infiltration of nervous tissue by lymphocytes, plasma cells, and macrophages, which cause destruction of the myelin sheaths that surround nerve cell axons in the brain and spinal cord. In some cases, EAE is induced by immunization of susceptible animals, such as mice, rats, guinea pigs, or non-human primates, with either myelin or various components of myelin. For example, EAE can be induced by immunization with components of the myelin sheath, such as myelin basic protein, proteolipid protein, or myelin oligodendrocyte glycoprotein (MOG). EAE is a useful and widely accepted model for studying mechanisms of autoimmune CNS tissue injury and for testing potential therapies for MS. EAE also includes "passive EAE" which is induced in the same manner in donor animals, but involves the transfer of activated T-cells harvested from the donor animal's lymph nodes to naïve recipient animals.

Inflammation: A localized protective response elicited by injury to tissue that serves to sequester the inflammatory agent. Inflammation is orchestrated by a complex biological response of vascular tissues to harmful stimuli, such as pathogens, damaged cells, or irritants. It is a protective attempt by the organism to remove the injurious stimuli as well as initiate the healing process for the tissue. An inflammatory response is characterized by an accumulation of white blood cells, either systemically or locally at the site of inflammation. The inflammatory response may be measured by many methods well known in the art, such as the number of white blood cells, the number of polymorphonuclear neutrophils (PMN), a measure of the degree of PMN activation, such as luminal enhanced chemiluminescence, or a measure of the amount of cytokines present. A primary inflammation disorder is a disorder that is caused by the inflammation itself. A secondary inflammation disorder is inflammation that is the result of another disorder. Inflammation can lead to a host of inflammatory diseases, including, but not limited to rheumatoid arthritis, osteoarthritis, inflammatory lung disease (including chronic obstructive pulmonary lung disease), inflammatory bowel disease (including ulcerative colitis and Crohn's Disease), periodontal disease, polymyalgia rheumatica, atherosclerosis, systemic lupus erythematosus, systemic sclerosis, Sjögren's Syndrome, asthma, allergic rhinitis, and skin disorders (including dermatomyositis and psoriasis) and the like. Autoimmune disorders which include an inflammatory component (including, but not limited to multiple sclerosis) are also considered to be inflammatory disorders.

Multiple sclerosis: An autoimmune disease classically described as a central nervous system white matter disorder disseminated in time and space that presents as relapsing-remitting illness in 80-85% of patients. Diagnosis can be made by brain and spinal cord magnetic resonance imaging (MRI), analysis of somatosensory evoked potentials, and analysis of cerebrospinal fluid to detect increased amounts of immunoglobulin or oligoclonal bands. MRI is a particularly sensitive diagnostic tool. MRI abnormalities indicating the presence or progression of MS include hyperintense white matter signals on T2-weighted and fluid attenuated inversion recovery images, gadolinium enhancement of active lesions, hypointensive "black holes" (representing gliosis and axonal pathology), and brain atrophy on T1-weighted studies. Serial MRI studies can be used to indicate disease progression. Relapsing-remitting multiple sclerosis (RRMS) is a clinical course of MS that is characterized by clearly defined, acute attacks with full or partial recovery and no disease progression between attacks. Secondary-progressive multiple sclerosis (SPMS) is a clinical course of MS that initially is relapsing-remitting, and then becomes progressive at a variable rate, possibly with an occasional relapse and minor remission. Primary progressive multiple sclerosis (PPMS) presents initially in the progressive form.

Neurodegenerative disease: Any type of disease or disorder that is associated with a progressive loss of motor, sensory and/or perceptual functions, and often involves behavioral and cognitive deficits. Neurodegenerative diseases are typically characterized by the progressive loss of structure or function of neurons, such as neurons within the cerebral cortex, basal ganglia, cerebellum, brain stem or motor systems. Neurodegenerative disorders include, but are not limited to, Alzheimer's disease, Parkinson's disease, Huntington's disease, ALS, multiple sclerosis, Lewy body dementia, vascular dementia, progressive supranuclear palsy, corticobasal degeneration, multiple system atrophy and frontotemporal dementia.

Neuroinflammation: Inflammation of the nervous tissue. Neuroinflammation can occur in response to a variety of different cues, including infection, traumatic brain injury, toxic metabolites, aging or autoimmunity (for example, multiple sclerosis). Neuroinflammation is typically chronic and results from sustained activation of glial cells and recruitment of other immune cells into the brain. The central nervous system is typically an immunologically privileged site because peripheral immune cells are generally blocked by the blood brain barrier (BBB). However, circulating peripheral immune cells may surpass a compromised BBB and encounter neurons and glial cells expressing major histocompatibility complex molecules, perpetuating the immune response.

Pharmaceutically acceptable carriers: The pharmaceutically acceptable carriers of use are conventional. Remington's Pharmaceutical Sciences, by E. W. Martin, Mack Publishing Co., Easton, Pa., 19th Edition, 1995, describes compositions and formulations suitable for pharmaceutical delivery of the compositions disclosed herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: Any chain of amino acids, regardless of length or posttranslational modification (such as glycosylation, methylation, ubiquitination, phosphorylation, or the like). In one embodiment, a polypeptide is a WE thrombin polypeptide. "Polypeptide" is used interchangeably with "protein," and is used to refer to a polymer of amino acid residues. A "residue" refers to an amino acid or amino acid mimetic incorporated in a polypeptide by an amide bond or amide bond mimetic.

Protein C activation cofactor: In the context of the present disclosure, a "protein C activation cofactor" is a molecule, such as a protein, that functions with thrombin (including WE thrombin) to activate protein C. In some embodiments herein, the protein C activation cofactor is thrombomodulin.

Recombinant: A recombinant nucleic acid or polypeptide is one that has a sequence that is not naturally occurring or has a sequence that is made by an artificial combination of two or more otherwise separated segments of sequence. This artificial combination is often accomplished by chemical synthesis or by the artificial manipulation of isolated segments of nucleic acids, e.g., by genetic engineering techniques.

Safe and effective amount: An amount of agent, such as a recombinant WE thrombin, that is sufficient to generate a desired response, such as reduce or eliminate a sign or symptom of a condition or disease, such as neuroinflammation. When administered to a subject, a dosage will generally be used that will achieve safe antithrombotic activity in primates, in vivo. In some examples, an "effective amount" is one that treats (including prophylaxis) one or more symptoms and/or underlying causes of any of an inflammatory and thrombotic disorder or disease, for example multiple sclerosis. An effective amount can be a therapeutically effective amount, including an amount that prevents one or more signs or symptoms of a particular disease or condition from developing, such as one or more signs or symptoms associated with neuroinflammation.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. Computer Appls. in the Biosciences 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site. BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost 5 of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity to a protein.

When aligning short peptides (fewer than around 30 amino acids), the alignment is performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, or 99% sequence identity to a protein. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. An alternative (and not necessarily cumulative) indication that two nucleic acid sequences are substantially identical is that the polypeptide which the first nucleic acid encodes is immunologically cross reactive with the polypeptide encoded by the second nucleic acid.

One of skill in the art will appreciate that the particular sequence identity ranges are provided for guidance only; it is possible that strongly significant homologs could be obtained that fall outside the ranges provided.

Subject: A living multicellular vertebrate organism, a category that includes, for example, mammals and birds. A "mammal" includes both human and non-human mammals, such as mice or non-human primates. In some examples, a subject is a patient, such as a patient that has or is at risk of developing multiple sclerosis.

Therapeutically effective amount: A dose sufficient to prevent advancement, or to cause regression of the disease, or which is capable of reducing symptoms caused by the disease, such as multiple sclerosis.

Thrombomodulin: An integral membrane protein expressed on the surface of endothelial cells that serves as a cofactor in the thrombin-induced activation of protein C. Thrombomodulin (TM) is also known as CD141 or BDCA-3.

Treating a disease: Inhibiting the full development of a disease or condition, for example, in a subject who has or who is at risk for a disease such as multiple sclerosis. "Treatment" refers to any therapeutic intervention that ameliorates a sign or symptom of a disease or pathological condition, such as neuroinflammation. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other clinical or physiological parameters associated with a particular disease. A "prophylactic" treatment is a treatment administered to a subject who does not exhibit signs of a disease or exhibits only early signs for the purpose of decreasing the risk of developing pathology. A "therapeutic" treatment is a treatment administered after the development of significant signs or symptoms of the disease.

WE Thrombin: A form of human thrombin comprising a mutation of the tryptophan (W) at residue 215 and the glutamate (E) at residue 217, including all homologs thereof with equivalent or similar activity. In some examples, the WE thrombin comprises a W→A mutation and/or an E→A mutation. One example of a WE thrombin sequence is SEQ ID NO: 1. *E coli* derived WE thrombin is an equivalent of WE thrombin produced by other methods; it may be interchangeably referred to as "EWE thrombin," "EWE," or "WE" herein. WE thrombin is described in detail in Gruber et al., U.S. Pat. No. 6,706,512, which is incorporated by reference herein. In some embodiments, the WE thrombin is at least 80%, at least 85%, at least 90%, at least 95%, at least 96%, at least 97%, at least 98% or at least 99% identical to SEQ ID NO: 1, and comprises an alanine (A) at positions 215 and 217. In particular examples, the WE thrombin comprises or consists of the amino acid sequence:

```
                                               (SEQ ID NO: 1)
TFGSGEADCGLRPLFEKKSLEDKTERELLESYIDGRIVEGSDAEIGM

SPWQVMLFRKSPQELLCGASLISDRWVLTAAHCLLYPPWDKNFTEND

LLVRIGKHSRTRYERNIEKISMLEKIYIHPRYNWRENLDRDIALMKL

KKPVAFSDYIHPVCLPDRETAASLLQAGYKGRVTGWGNLKETWTANV

GKGQPSVLQVVNLPIVERPVCKDSTRIRITDNMFCAGYKPDEGKRGD

ACEGDSGGPFVMKSPFNNRWYQMGIVSAGAGCDRDGKYGFYTHVFRL

KKWIQKVIDQFGE.
```

III. Introduction

The use of APC infusion to treat neuroinflammation has the potential to cause bleeding as it leads to systemic antihemostatic anticoagulation. However, activation of the endogenous protein C using a protein C activator compound could overcome this shortcoming of APC, heparin, or other fluid phase anticoagulants. The effect of these activators is confined to the intraluminal surface of blood vessels, where endogenous protein C is located, bound to its receptor, EPCR. The protein C activator enzyme WE thrombin and homologs thereof, as well as activation cofactors, such as soluble thrombomodulin, are disclosed herein as a safe alternative to recombinant APC or other anticoagulants.

WE (W215A/E217A) thrombin is a human recombinant thrombin analog that contains two mutations, generating a molecule with significantly reduced procoagulant activity. Human WE thrombin activity toward human fibrinogen and PAR-1 is reduced 19,000 and 1,200 fold, respectively (Cantwell and Di Cera, *J Biol Chem* 275:39827-39830, 2000; and Gruber et al, U.S. Pat. No. 6,706,512, which is herein incorporated by reference). WE thrombin retains 10% of the thrombomodulin-dependent anticoagulant function of thrombin. Due to this re-design of the molecule, WE thrombin selectively activates protein C in the presence of its cofactor, thrombomodulin, to form APC. Administration of WE thrombin to non-human primates has been shown to cause activation of endogenous protein C and inhibit acute vascular graft thrombosis without any signs of wound bleeding or other adverse events. Likewise, administration of its cofactor, thrombomodulin, is antithrombotic in the same model by supporting the activation of surface-associated protein C on the endothelial protein C receptors (EPCR), also including apoER2. The concentration of APC detected in the plasma after administration of WE thrombin or thrombomodulin is significantly lower than the concentration of exogenous APC required to produce an equivalent anticoagulant effect. This is a significant safety advantage of endogenous protein C activation over APC administration, because it reduces the risk of bleeding from protein C activator treatment, compared to administration of recombinant APC or other conventional anticoagulants which are inherently anti-hemostatic because they are in the fluid phase.

IV. Methods of Treating Neuroinflammation

Disclosed herein are methods of treating neuroinflammation in a subject. In some embodiments, the method includes selecting a subject with neuroinflammation and administering to the subject an effective amount of WE thrombin, thereby treating the neuroinflammation. Further disclosed are methods of treating multiple sclerosis in a subject, comprising selecting a subject with multiple sclerosis and administering to the subject an effective amount of WE thrombin, thereby treating the multiple sclerosis. In some embodiments, the method includes intravenous administration of the WE thrombin. In some embodiments, the method involves the administration of a dosage of at least 25 µg/kg of WE thrombin. In some examples, the method includes the use of WE thrombin derived from expression in $E.\ coli$.

Also provided are methods of treating an inflammatory and/or autoimmune disease or disorder in a subject by administering recombinant WE thrombin. In some embodiments the inflammatory and/or autoimmune disease or disorder is systemic lupus erythematosus, Sjögren's syndrome, rheumatoid arthritis, type I diabetes mellitus, Wegener's granulomatosis, inflammatory bowel disease, polymyositis, dermatomyositis, multiple endocrine failure, Schmidt's syndrome, autoimmune uveitis, celiac disease, Addison's disease, adrenalitis, Graves' disease, thyroiditis, Hashimoto's thyroiditis, autoimmune thyroid disease, pernicious anemia, gastric atrophy, chronic hepatitis, lupoid hepatitis, atherosclerosis, presenile dementia, demyelinating diseases, subacute cutaneous lupus erythematosus, hypoparathyroidism, Dressler's syndrome, myasthenia gravis, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), adult onset diabetes mellitus (type II diabetes), male and female autoimmune infertility, ankylosing spondylitis, ulcerative colitis, Crohn's disease, mixed connective tissue disease, polyarteritis nedosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, allergic disease, allergic encephalomyelitis, toxic epidermal necrolysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, glomerulonephritis, graft versus host disease, transplantation rejection, human immunodeficiency virus infection, echovirus infection, cardiomyopathy, Alzheimer's disease, parvovirus infection, rubella virus infection, post vaccination syndromes, congenital rubella infection, Hodgkin's and Non-Hodgkin's lymphoma, renal cell carcinoma, multiple myeloma, Eaton-Lambert syndrome, relapsing polychondritis, malignant melanoma, cryoglobulinemia, Waldenstrom's macroglobulemia, Epstein-Barr virus infection, rubulavirus, or 5 Evan's syndrome.

Additional inflammatory diseases that can be treated include osteoarthritis, inflammatory lung disease (including chronic obstructive pulmonary lung disease), periodontal disease, polymyalgia rheumatica, atherosclerosis, systemic sclerosis, allergic rhinitis, and skin disorders (including dermatomyositis and psoriasis) and the like.

In other embodiments, the subject has a retinal disorder, such as a retinal degeneration, such as retinitis pigmentosa, cone-rod dystrophy, Leber congenital amaurosis, or a maculopathy (for example, age-related macular degeneration, Stargardt-like macular degeneration, vitelliform macular dystrophy (Best disease), Malattia Leventinese (Doyne's honeycomb retinal dystrophy), diabetic maculopathy, occult macular dystrophy, or cellophane maculopathy. In other examples, a retinal disorder includes a retinopathy, such as autoimmune retinopathy, diabetic retinopathy, or vascular retinopathy. In still further examples, a retinal disorder includes retinal detachment or glaucoma. Retinal disorders may be progressive (for example, retinal degeneration or glaucoma) or acute (for example, retinal detachment). In additional examples, the subject is a subject with uveitis or optic neuritis. In other embodiments, the subject has had a stroke (such as ischemic stroke or hemorrhagic stroke). In still further examples, the subject is a subject with substance addiction, for example, a subject with cognitive or neuropsychiatric impairment induced by substance addiction including methamphetamine and alcohol abuse.

In particular embodiments, provided is a method of treating neuroinflammation in a subject, the method comprising administering to the subject a pharmaceutical composition comprising a safe and effective amount of recombinant WE thrombin, or a homolog thereof. In some examples, the method further includes the step of selecting a subject with neuroinflammation. The neuroinflammation can result from any one of a number of different diseases, disorders or environmental conditions, such as infection, traumatic brain injury, toxic metabolites, aging or autoimmunity (for example, multiple sclerosis). In some examples, the neuroinflammation comprises encephalopathy or demyelination. In particular non-limiting examples, the subject has multiple sclerosis.

In some embodiments of the disclosed methods, the amino acid sequence of the WE thrombin is at least 80%, at least 85%, at least 90%, at least 95%, at least 96%, at least 97%, at least 98% or at least 99% identical to SEQ ID NO: 1 and comprises an alanine at positions 215 and 217. In particular examples, the amino acid sequence of the WE thrombin comprises or consists of SEQ ID NO: 1.

In some embodiments, the pharmaceutical composition is formulated to be administered intravenously.

In some embodiments, the subject is a primate and the pharmaceutical composition is formulated to deliver a total dose of at least 1.25 µg/kg WE thrombin.

In some embodiments, the recombinant WE thrombin is derived from expression in *E. coli*.

In some embodiments, the subject is further administered one or more protein C activation cofactors. In particular examples, the one or more protein C activation cofactors comprises thrombomodulin, such as recombinant soluble human thrombomodulin.

The WE thrombin can be formulated with an appropriate solid or liquid carrier depending on the mode of administration chosen.

V. Pharmaceutical Compositions

Disclosed herein are pharmaceutical compositions for use in treating neuroinflammation in a subject, such as a subject with multiple sclerosis. The pharmaceutical compositions comprise an effective amount of WE thrombin. In some embodiments, the pharmaceutical composition is formulated to be administered intravenously. In some embodiments, the pharmaceutical composition is formulated to deliver a dose of 25 μg/kg recombinant WE thrombin. In some examples, the pharmaceutical composition comprises *E. coli* derived WE thrombin.

Provided herein is a pharmaceutical composition for use in treating neuroinflammation in a subject. In some embodiments, the pharmaceutical composition includes an effective amount of recombinant WE thrombin, or a homolog thereof; and a pharmaceutically acceptable carrier.

In some embodiments, the amino acid sequence of the WE thrombin is at least 80%, at least 85%, at least 90%, at least 95%, at least 96%, at least 97%, at least 98% or at least 99% identical to SEQ ID NO: 1 and comprises an alanine at positions 215 and 217. In particular examples, the amino acid sequence of the WE thrombin comprises or consists of SEQ ID NO: 1.

In some embodiments, the pharmaceutical composition is formulated to be administered intravenously.

In some embodiments, the subject is a primate and the pharmaceutical composition is configured to deliver a total dose of at least 1.25 μg/kg WE thrombin.

In some embodiments, the recombinant WE thrombin is derived from expression in *E. coli*.

In some embodiments, the neuroinflammation comprises encephalopathy or demyelination.

In some embodiments, the pharmaceutical composition is for use in treating a subject with multiple sclerosis.

In some embodiments, the pharmaceutical composition further comprises one or more protein C activation cofactors. In some examples, the one or more cofactors comprises thrombomodulin, such as recombinant soluble human thrombomodulin.

In some embodiments, a subject is administered an effective amount of a composition comprising recombinant WE thrombin or an effective portion thereof. Pharmaceutical compositions comprising the recombinant polypeptide disclosed herein can be formulated with an appropriate solid or liquid carrier, depending upon the particular mode of administration chosen. The pharmaceutically acceptable carriers and excipients useful in this disclosure are conventional (see, e.g., Remington: The Science and Practice of Pharmacy, The University of the Sciences in Philadelphia, Editor, Lippincott, Williams, & Wilkins, Philadelphia, Pa., 21st Edition (2005). For instance, parenteral formulations usually include injectable fluids that are pharmaceutically and physiologically acceptable fluid vehicles such as water, physiological saline, other balanced salt solutions, aqueous dextrose, glycerol or the like. For solid compositions (e.g., powder, pill, tablet, or capsule forms), conventional non-toxic solid carriers can include, for example, pharmaceutical grades of mannitol, lactose, starch, or magnesium stearate.

In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate. Excipients that can be included are, for instance, other proteins, such as human serum albumin or plasma preparations. The dosage form of the pharmaceutical composition will be determined by the mode of administration chosen. For instance, in addition to injectable fluids, topical, inhalation, oral and suppository formulations can be employed. Topical preparations can include eye drops, ointments, sprays, patches and the like. Inhalation preparations can be liquid (for example, solutions or suspensions) and include mists, sprays and the like. Oral formulations can be liquid (for example, syrups, solutions or suspensions), or solid (for example, powders, pills, tablets, or capsules). Suppository preparations can also be solid, gel, or in a suspension form. For solid compositions, conventional non-toxic solid carriers can include pharmaceutical grades of mannitol, lactose, starch, or magnesium stearate. Actual methods of preparing such dosage forms are known, or will be apparent, to those skilled in the art.

In some examples, the pharmaceutical composition is administered by any mode that achieves its intended purpose. Amounts and regimens for the administration of the recombinant polypeptides or portion thereof (or a nucleic acid encoding such polypeptides) can be determined by the attending clinician. Effective doses for therapeutic application will vary depending on the nature and severity of the condition to be treated, the age and condition of the patient, and other clinical factors. In some cases, the dose range will be from about 0.1 μg/kg body weight to about 100 mg/kg body weight. Other suitable ranges include doses of from about 10 μg/kg to about 50 mg/kg body weight, about 20 μg/kg to about 25 mg/kg body weight, including 25 μg/kg or more. The dosing schedule may vary from once a week to daily depending on a number of clinical factors, such as the subject's sensitivity to the protein. The pharmaceutical compositions that include the disclosed recombinant WE thrombin can be formulated in unit dosage form, suitable for individual administration of precise dosages. In one specific, non-limiting example, a unit dosage can contain from about 1 ng to about 5 g of the recombinant polypeptide (such as about 10 μg to 1 g or about 10 mg to 100 mg). The amount of active compound(s) administered will be dependent on the subject being treated, the severity of the affliction, and the manner of administration. Within these bounds, the formulation to be administered will contain a quantity of the active component(s) in amounts effective to achieve the desired effect in the subject being treated.

The recombinant WE thrombin can be administered to humans or other animals on whose tissues they are effective in various manners such as topically, orally, intravenously, intramuscularly, intraperitoneally, intranasally, intradermally, intrathecally, subcutaneously, intraocularly, via inhalation, or via suppository. In one example, the compounds are administered to the subject subcutaneously. In another example, the compounds are administered to the subject intravenously.

In some embodiments, the recombinant WE thrombin is included in an inert matrix for topical application. In some examples, the formulation is injected into the eye, for example for intravitreal injection. As one example of an inert matrix, liposomes may be prepared from dipalmitoyl phosphatidylcholine (DPPC), such as egg phosphatidylcholine (PC). Liposomes, including cationic and anionic liposomes, can be made using standard procedures as known to one skilled in the art. Liposomes including the recombinant WE thrombin can be applied topically, either in the form of drops or as an aqueous based cream, or can be injected intraocularly. In a formulation for topical application, the recombinant WE thrombin is slowly released over time as the liposome capsule degrades due to wear and tear from the eye surface. In a formulation for intraocular injection, the liposome capsule degrades due to cellular digestion. Both of these formulations provide advantages of a slow release drug delivery system, allowing the subject to be exposed to a substantially constant concentration of the recombinant WE thrombin over time. In one example, the recombinant WE thrombin can be included in a delivery system that can be implanted at various sites in the eye, depending on the size, shape and formulation of the implant, and the type of transplant procedure. Suitable sites include but are not limited to the anterior chamber, anterior segment, posterior chamber, posterior segment, vitreous cavity, suprachoroidal space, subconjunctiva, episcleral, intracorneal, epicorneal and sclera.

In some examples, an effective amount (for example, a therapeutically effective amount) of a disclosed recombinant WE thrombin can be the amount of WE thrombin necessary to treat or inhibit a disorder (such as an inflammatory and/or autoimmune disorder) in a subject. In other examples, a therapeutically effective amount of a disclosed WE thrombin can be the amount of WE thrombin necessary to treat or inhibit a retinal disorder, stroke, or disorders associated with substance addiction (such as cognitive or neuropsychiatric impairment resulting from substance addiction).

The present disclosure also includes combinations of the recombinant WE thrombin with one or more other agents useful in the treatment of a disorder. In some examples, the recombinant WE thrombin can be administered with effective doses of one or more therapies for inflammatory or autoimmune disorders, including but not limited to non-steroidal anti-inflammatory drugs, corticosteroids, methotrexate, anti-TNF compounds, mycopheonlate, aminoslicylates, antibiotics, interferons, glatiramer acetate, antibody therapies (such as rituximab or milatuzumab), or immunosuppressant or immunomodulator compounds. In another example, the recombinant polypeptides can be administered in combination with effective doses of one or more therapies for retinal disorders, including but not limited to, gene therapy, vitamin or mineral supplements (such as vitamins A, C, and/or E, or zinc and/or copper), anti-angiogenic therapy (such as ranibizumab or bevacizumab), photocoagulation, photodynamic therapy, lutein or zeaxanthin, corticosteroids, or immunosuppressants. Appropriate combination therapy for a particular disease can be selected by one of ordinary skill in the art. The term "administration in combination" or "co-administration" refers to both concurrent and sequential administration of the active agents.

The following examples are provided to illustrate certain particular features and/or embodiments. These examples should not be construed to limit the disclosure to the particular features or embodiments described.

EXAMPLES

The following examples are illustrative of disclosed methods. In light of this disclosure, those of skill in the art will recognize that variations of these examples and other examples of the disclosed method would be possible without undue experimentation.

Example 1—Experimental Procedures

This example describes the materials and experimental procedures for the studies described in Examples 2-5.

Expression and Purification of WE Thrombin

Human WE (W215A/E217A) prethrombin-2 (SEQ ID NO: 1) was expressed in *E. Coli* as inclusion bodies. Following lysis of inclusion bodies, the prethrombin-2 precursor was refolded, purified by affinity chromatography on heparin SEPHAROSE™, activated by proteolytic cleavage using ecarin and further purified by heparin and ion exchange chromatography. The protein solution was treated with Detoxi-gel Endotoxin Removing Gel (Pierce) to remove potential endotoxin contamination. The Detoxi-gel treated pool was subsequently concentrated and diafiltered into 20 mM Tris, 300 mM NaCl, pH 8 for storage. Enzymatic activity of the resulting protein towards protein C was assessed using a chromogenic assay.

Induction of Active EAE and Treatment with WE Thrombin

EAE was induced using mouse myelin oligodendrocyte glycoprotein (MOG) residues 35-55 ($MOG_{35-55}$). $MOG_{35-55}$ was combined with complete Freund's adjuvant containing heat-inactivated *M. tuberculosis* as previously described. All mice were injected with 75 ng and 200 ng pertussis toxin (Ptx) intraperitoneally on days 0 and 2 relative to immunization. The mice were assessed for signs of EAE according to the following scale: 0, normal; 1, limp tail or mild hindlimb weakness; 2, moderate hindlimb weakness or mild ataxia; 3, moderately severe hindlimb weakness; 4, severe hindlimb weakness or mild forelimb weakness or moderate ataxia; 5, paraplegia with no more than moderate forelimb weakness; and 6, paraplegia with severe forelimb weakness or severe ataxia or moribund condition. At the onset of clinical signs of EAE (between days 10-13 when the clinical scores were ≥2), mice were divided into two groups and treated with either saline control or with 25 μg/kg WE-thrombin intravenously. Mice were monitored for changes in disease score until they were euthanized for ex vivo analyses.

Fluorescence-Activated Cell-Sorting (FACS)

Four-color fluorescence flow cytometry analyses were performed to determine the phenotypes of cells following general antibody staining procedures. For splenocytes, single cell suspensions of spleens were prepared by homogenizing the tissue through a fine mesh screen. Mononuclear cells from the CNS were isolated by PERCOLL™ gradient centrifugation. Cells ($10^6$) were washed with staining medium (PBS containing 0.1% $NaN_3$ and 1% bovine serum albumin; Sigma) and incubated with combinations of the following monoclonal antibodies: CD4, CD45, ICAM-1 and CD11b, for phenotype analysis.

Immunohistochemistry

Mice were deeply anesthetized with isoflurane, heparinized and perfused with 100 ml of 4% paraformaldehyde in 0.1 M sodium phosphate buffer (pH 7.4), and fixed at 4° C. for 24 hours. The spinal cords were dissected from the spinal columns and sections 1-2 mm in length sampled from the thoracic and lumbar region. Tissues were fixed in 5% glutaraldehyde in 0.1 M sodium phosphate buffer (pH 7.4) for three days at 4° C., post-fixed with 1% osmium tetroxide for 3.5 hours, rehydrated in ethanol, and embedded in plastic. Semi-thin sections (0.5 µm) were stained with toluidine blue and photographed under a light microscope. Images were compiled to create a complete construction of the entire spinal cord section. Stained tissue sections were analyzed by an investigator blinded to treatment status and axonal damage and demyelination determined.

Immunofluorescence

Fibrin(ogen) deposition in lumbar sections was detected using a rabbit polyclonal antibody against human fibrin (ogen). Sections were fixed, embedded in paraffin, sectioned, and dewaxed. Slides were blocked in 10% NGS, 1% BSA, 0.025% triton-X for 45 minutes at room temperature, followed by incubation with a rabbit polyclonal antibody to fibrin(ogen) (MP Biomedicals, LLC) overnight at 4° C., diluted 1:50 in goat serum, and then incubated with goat anti-rabbit IgG (Molecular Probes; ALEXA FLUOR™488). Slides were washed and mounted under aqueous media. Negative control slides were treated as above without primary antibody. Sections were photographed under 20× and images processed under identical conditions using Slidebook.

Analysis of fibrin(ogen) was performed using the following method. Fluorescence intensity in a 10-µm$^2$, non-cellular region was measured, averaged to yield a mean background fluorescence and subtracted from every image. Fibrin(ogen) signal intensity was thresholded by measuring nonspecific staining in a negative control (absence of primary antibody). This value was used to set the lower limit of the calibration scale for all subsequent measurements. Thus, only fluorescence above background and separate from nonspecific staining was visualized. Images were compiled in Photoshop to create complete construction of the entire spinal cord section. Fibrin(ogen) staining in representative lumbar sections was evaluated by measuring the total area of the spinal cord section in um$^2$. The area of positive signal above threshold within this area was subsequently measured to determine the % area positive for signal and the total signal per µm$^2$.

Statistical Analysis

All data are expressed as means±SEM. Statistical difference between vehicle and treatment group for disease score was evaluated by Mann-Whitney U test. Cumulative disease index, cell frequency and fibrin(ogen) content in lumbar sections were analyzed using student's t-test. A p-value of less than 0.05 was considered significant. Statistical analyses were made using GraphPad Prism version 5.01 for Windows, GraphPad Software, San Diego Calif. USA.

Example 2—WE Thrombin Reverses Clinical Signs of EAE

Figure 1B:
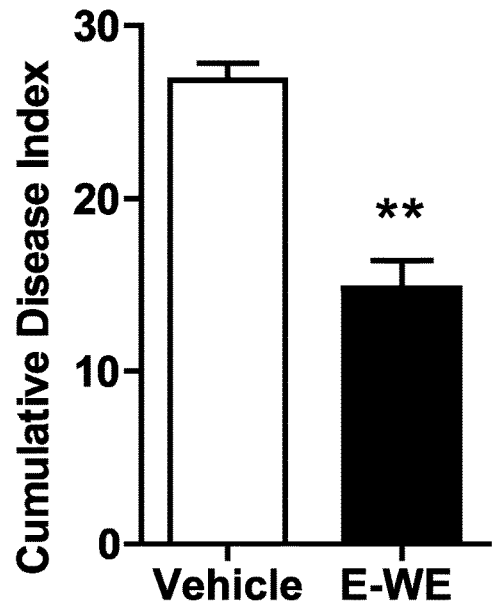
FIG. 1B is a bar graph of the cumulative disease index showing that the cumulative disease index for E-WE thrombin treated mice was significantly lower than that of vehicle treated mice. Data presented are the means+/−SEM of two independent experiments, with n=7-10, from which three mice per group were sampled for ex vivo analysis. Significant differences between vehicle and E-WE treated groups were determined using unpaired t-test, p<0.01.

To evaluate the efficacy of E-WE administration following the onset of clinical signs of EAE (day 10-13), mice were treated daily with either 100 µl of vehicle or E-WE thrombin (25 µg/ml; intravenously) and monitored for 8 days. Compared with vehicle-treated control mice, performance scores for E-WE-treated mice were significantly improved (FIG. 1A). Control mice had a cumulative disease index (CDI) of 27.4±2.2, whereas E-WE-treated mice demonstrated a significantly reduced CDI of 14.3±2.2 (FIG. 1B). The peak disease score for E-WE-treated mice was also significantly reduced as compared to vehicle-treated mice (3.7±0.2 vs 2.5±0.2; p<0.05).

Example 3—WE Thrombin Reduces Inflammatory Markers in EAE

Figure 2A:
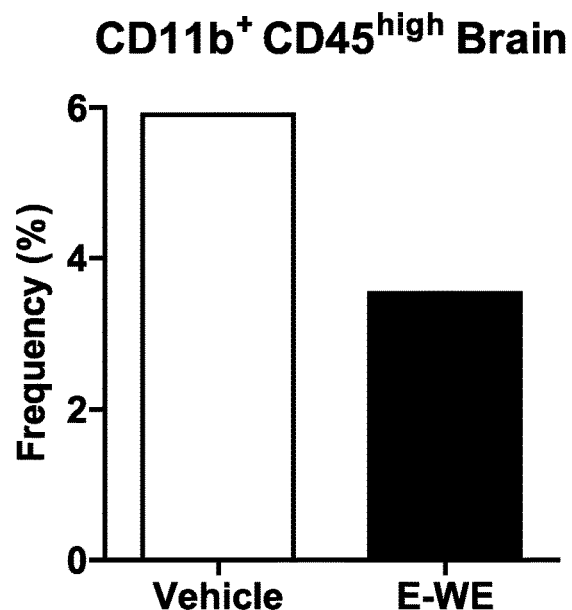
FIG. 2A is a bar graph showing the frequency of CD11b$^+$CD45$^{high}$ cells in E-WE thrombin and vehicle treated mice, measured by FACS analysis. Data represent pooled CNS cells from five mice.
Figure 2B:
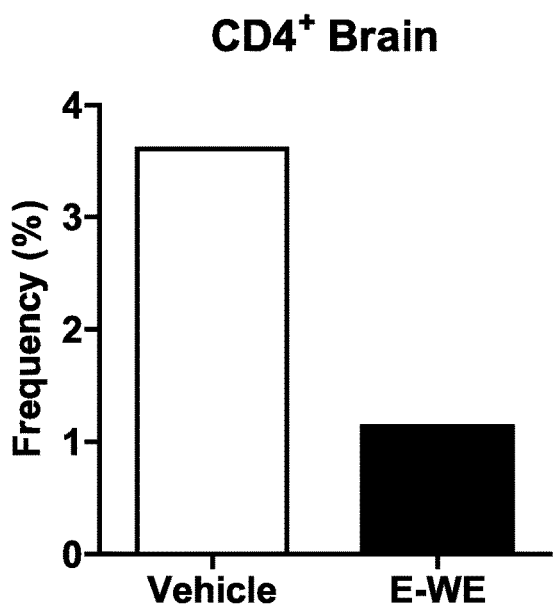
FIG. 2B is a bar graph showing the frequency of CD4$^+$ cells in E-WE thrombin and vehicle treated mice, measured by FACS analysis. Data represent pooled CNS cells from five mice.
Figure 3A:
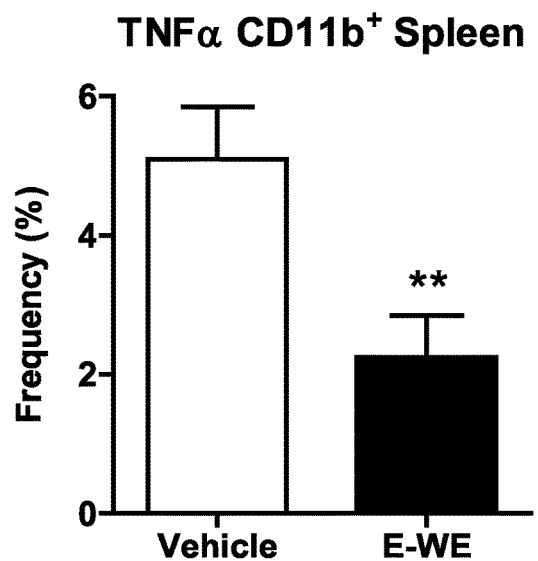
FIG. 3A is a bar graph showing TNFα$^+$ macrophages in E-WE thrombin and vehicle treated mice. Mice were sacrificed on day 30 and splenocytes subjected to FACS analysis. To evaluate the macrophage subpopulation, cells were gated for CD11b$^+$. Data are the means+/−SEM of n=3 mice. Significant difference between vehicle and E-WE treated groups were determined using unpaired t-test,*p<0.01.
Figure 3B:
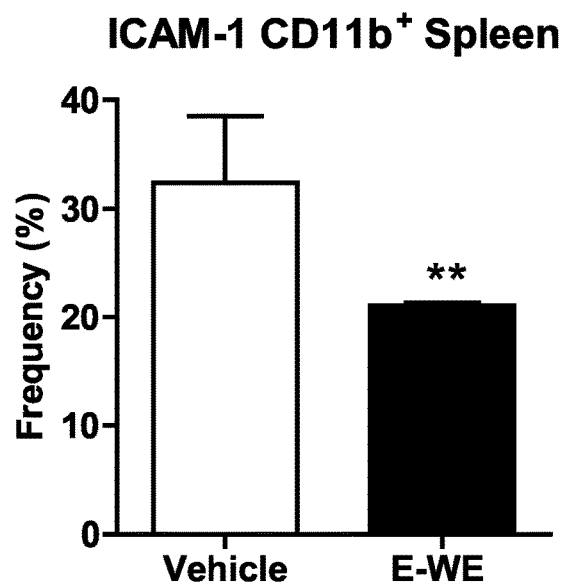
FIG. 3B is a bar graph showing ICAM-1$^+$ macrophages in E-WE thrombin and vehicle treated mice. Mice were sacrificed on day 30 and splenocytes subjected to FACS analysis. To evaluate the macrophage subpopulation, cells were gated for CD11b$^+$. Data are the means+/−SEM of n=3 mice. Significant difference between vehicle and E-WE treated groups were determined using unpaired t-test,*p<0.01.

Because microgliosis is a hallmark of CNS inflammation, the identity and quantity of mononuclear cells in pooled brains of vehicle- and E-WE-treated mice was determined. E-WE-treatment significantly reduced the absolute number of macrophages (CD11b/CD45 high cells) from 18880 to 9912 cells in vehicle vs. WE-treated mice, respectively (Table 1). The frequency of CD11b/CD45 high cells decreased from 5.9% to 3.5% in vehicle vs. E-WE-treated mice, respectively (FIG. 2A). Furthermore, treatment with E-WE reduced both the absolute number and percentage of CD4+ cells in the brain (FIG. 2B and Table 1). Additionally, treatment with E-WE reduced both TNFα and ICAM-1 expression on CD11b$^+$ macrophages in EAE (FIGS. 3A and 3B). Collectively, these results demonstrate that E-WE reduces the inflammatory markers in the brain and spleen of mice during EAE.

TABLE 1

Effect of E-WE thrombin treatment on inflammatory cells in the brain Absolute Cell Number in Pooled Brain (n = 5)

| Cell type | Vehicle | E-WE thrombin |
| --- | --- | --- |
| CD11b$^+$/CD45$^{high}$ | 18880 | 9912 |
| CD4$^+$ | 11552 | 3192 |

Example 4—WE Thrombin Reduces CNS Pathology in Mice Immunized with MOG35-55

Figure 4A:
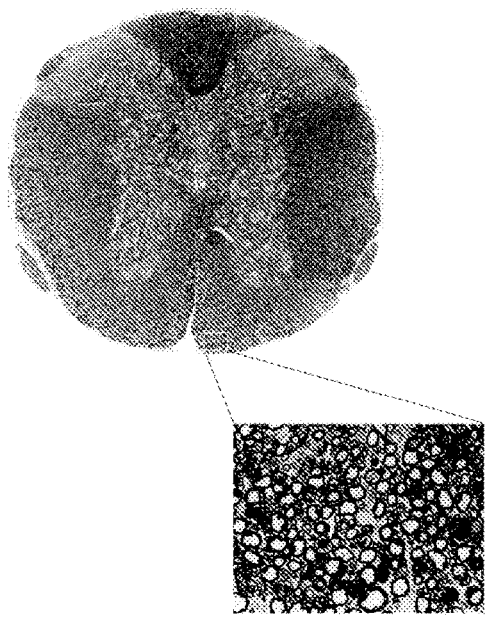
FIG. 4A is an image of a thoracic spinal cord from a vehicle treated mouse. Spinal cords were stained with toluidine blue and assessed for axonal damage. Mice were immunized with MOG and treated as indicated. Areas of tissue damage are circled and the white rectangles demarcate area magnified and presented below.
Figure 4B:
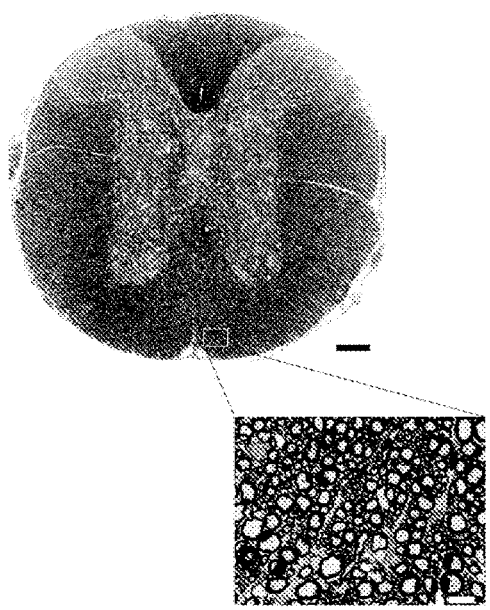
FIG. 4B is an image of a thoracic spinal cord from an E-WE thrombin treated mouse. Spinal cords were stained with toluidine blue and assessed for axonal damage. Mice were immunized with MOG and treated as indicated. Areas of tissue damage are circled and the white rectangles demarcate area magnified and presented below. In whole sections, scale bar is 100 µm and in high power view, scale bar is 10 µm.

The efficacy of WE to reduce axonal damage and demyelination in spinal cord tissue was also determined. Consistent with the pathology associated with EAE, the spinal cords of vehicle-treated mice showed intense subpial and perivascular inflammation and demyelination (FIG. 4). Spinal cords of mice treated with WE showed a dramatic decrease in infiltrating cells and demyelination.

Example 5—Fibrin(ogen) Deposition

Figure 5A:
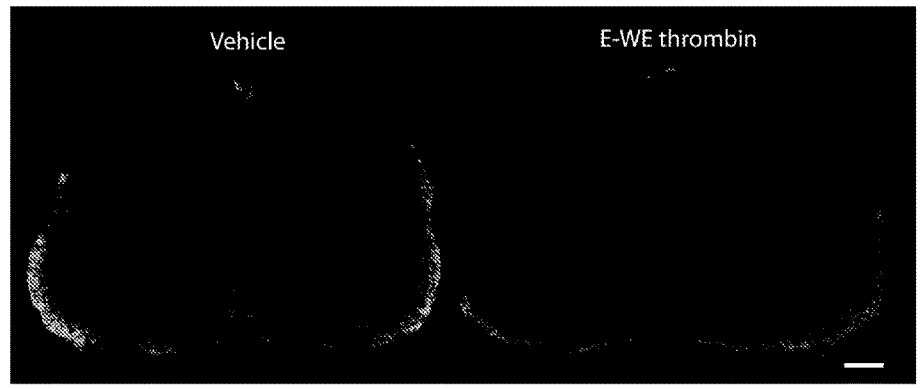
FIG. 5A is an image of lumbar spinal cords from mice treated with vehicle (left) and E-WE thrombin (right). Spinal cords were labeled with an antibody specific for fibrin(ogen). Scale bar is 100 µM.
Figure 5B:
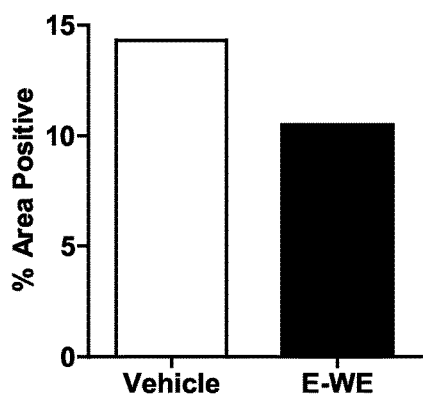
FIG. 5B is a bar graph of the area of positive signal from spinal cord sections labeled as shown in FIG. 5A relative to the entire area of the section.
Figure 5C:
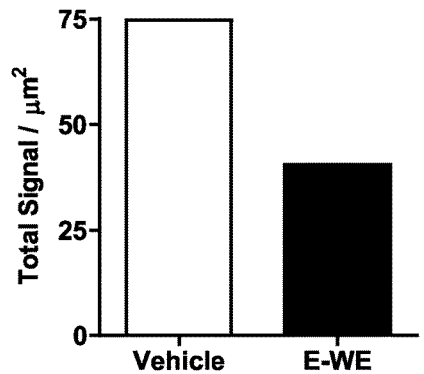
FIG. 5C is a bar graph of the total area of positive signal in spinal cord sections labeled as shown in FIG. 5A.

Immunofluorescence revealed positive staining for fibrin (ogen) in the lumbar spinal cord of a vehicle treated mouse. Distribution of fibrin(ogen) in spinal cord sections was consistent with previous data demonstrating fibrin in white matter of EAE mice. Compared to vehicle control, there appeared to be reduced signal for fibrin(ogen) in E-WE treated mice (FIG. 5A). To quantify fibrin(ogen), the percent of area positive was measured. The data indicated that fibrin(ogen) staining was reduced from 14.3% in vehicle to 10.5% in E-WE (FIG. 5B). Similarly, the total signal area per µm$^2$ was reduced to nearly half from 74.7 to 40.5 in vehicle and E-WE groups, respectively (FIG. 5C).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of treating neuroinflammation in a subject, the method comprising:

administering to the subject a pharmaceutical composition comprising a safe and effective amount of recombinant WE thrombin, or a homolog thereof.

2. The method of claim 1, wherein the amino acid sequence of the WE thrombin is at least 95% identical to SEQ ID NO: 1 and comprises an alanine at positions 215 and 217.

3. The method of claim 1, wherein the amino acid sequence of the WE thrombin is at least 99% identical to SEQ ID NO: 1 and comprises an alanine at positions 215 and 217.

4. The method of claim 1, wherein the amino acid sequence of the WE thrombin comprises or consists of SEQ ID NO: 1.

5. The method of claim 1, wherein the pharmaceutical composition is formulated to be administered intravenously.

6. The method of claim 1, wherein the subject is a primate and the pharmaceutical composition is formulated to deliver a total dose of at least 1.25 µg/kg WE thrombin.

7. The method of claim 1, wherein the recombinant WE thrombin is derived from expression in *E. coli*.

8. The method of claim 1, wherein the neuroinflammation comprises encephalopathy or demyelination.

9. The method of claim 1, wherein the subject has multiple sclerosis.

10. The method of claim 1, further comprising administering one or more protein C activation cofactors to the subject.

11. The method of claim 10, wherein the one or more cofactors comprises thrombomodulin.

12. The method of claim 11, wherein the thrombomodulin is recombinant soluble human thrombomodulin.

* * * * *

SEQUENCE LISTING

```
<160> NUMBER OF SEQ ID NOS: 1

<210> SEQ ID NO 1
<211> LENGTH: 295
<212> TYPE: PRT
<213> ORGANISM: Artificial Sequence
<220> FEATURE:
<223> OTHER INFORMATION: Synthetic polypeptide

<400> SEQUENCE: 1

Thr Phe Gly Ser Gly Glu Ala Asp Cys Gly Leu Arg Pro Leu Phe Glu
1               5                   10                  15

Lys Lys Ser Leu Glu Asp Lys Thr Glu Arg Glu Leu Leu Glu Ser Tyr
            20                  25                  30

Ile Asp Gly Arg Ile Val Glu Gly Ser Asp Ala Glu Ile Gly Met Ser
        35                  40                  45

Pro Trp Gln Val Met Leu Phe Arg Lys Ser Pro Gln Glu Leu Leu Cys
50                  55                  60

Gly Ala Ser Leu Ile Ser Asp Arg Trp Val Leu Thr Ala Ala His Cys
65                  70                  75                  80

Leu Leu Tyr Pro Pro Trp Asp Lys Asn Phe Thr Glu Asn Asp Leu Leu
                85                  90                  95

Val Arg Ile Gly Lys His Ser Arg Thr Arg Tyr Glu Arg Asn Ile Glu
                100                 105                 110

Lys Ile Ser Met Leu Glu Lys Ile Tyr Ile His Pro Arg Tyr Asn Trp
            115                 120                 125

Arg Glu Asn Leu Asp Arg Asp Ile Ala Leu Met Lys Leu Lys Lys Pro
        130                 135                 140

Val Ala Phe Ser Asp Tyr Ile His Pro Val Cys Leu Pro Asp Arg Glu
145                 150                 155                 160

Thr Ala Ala Ser Leu Leu Gln Ala Gly Tyr Lys Gly Arg Val Thr Gly
                165                 170                 175

Trp Gly Asn Leu Lys Glu Thr Trp Thr Ala Asn Val Gly Lys Gly Gln
                180                 185                 190

Pro Ser Val Leu Gln Val Val Asn Leu Pro Ile Val Glu Arg Pro Val
            195                 200                 205

Cys Lys Asp Ser Thr Arg Ile Arg Ile Thr Asp Asn Met Phe Cys Ala
210                 215                 220

Gly Tyr Lys Pro Asp Glu Gly Lys Arg Gly Asp Ala Cys Glu Gly Asp
225                 230                 235                 240

Ser Gly Gly Pro Phe Val Met Lys Ser Pro Phe Asn Asn Arg Trp Tyr
                245                 250                 255

Gln Met Gly Ile Val Ser Ala Gly Ala Gly Cys Asp Arg Asp Gly Lys
            260                 265                 270

Tyr Gly Phe Tyr Thr His Val Phe Arg Leu Lys Lys Trp Ile Gln Lys
        275                 280                 285

Val Ile Asp Gln Phe Gly Glu
    290                 295
```